(12) United States Patent
Hendriks et al.

(10) Patent No.: US 11,474,095 B2
(45) Date of Patent: Oct. 18, 2022

(54) DEVICE FOR ASSESSING CHANGES IN ERYTHROCYTE DEFORMABILITY, SUCH AS ERYTHROCYTE SICKLING TENDENCY

(71) Applicant: R&R Mechatronics International B.V., Zwaag (NL)

(72) Inventors: Sisto Hendriks, Zwaag (NL); Juan Pedro De Zoeten, Zwaag (NL); Hans Van De Bospoort, Zwaag (NL)

(73) Assignee: R&R Mechatronics International B.V., Zwaag (NL)

( * ) Notice: Subject to any disclaimer, the term of this patent is extended or adjusted under 35 U.S.C. 154(b) by 402 days.

(21) Appl. No.: 16/647,789

(22) PCT Filed: Oct. 24, 2018

(86) PCT No.: PCT/EP2018/079091
§ 371 (c)(1),
(2) Date: Mar. 16, 2020

(87) PCT Pub. No.: WO2019/081547
PCT Pub. Date: May 2, 2019

(65) Prior Publication Data
US 2020/0217836 A1    Jul. 9, 2020

(30) Foreign Application Priority Data
Oct. 26, 2017   (NL) .................................... 2019813

(51) Int. Cl.
*G01N 33/49*   (2006.01)
*A61B 5/1455*   (2006.01)
*G01N 21/53*   (2006.01)

(52) U.S. Cl.
CPC ..... *G01N 33/4925* (2013.01); *A61B 5/14552* (2013.01); *G01N 21/534* (2013.01)

(58) Field of Classification Search
CPC .. A61B 5/14552; G01N 11/14; G01N 21/534; G01N 2203/0089; G01N 33/49; G01N 33/4925
(Continued)

(56) References Cited

U.S. PATENT DOCUMENTS 4,997,769 A * 3/1991 Lundsgaard ........... G01N 21/31
436/66

OTHER PUBLICATIONS

Stozicky et al., An improved diffractometric method for measurement of cellular deformability, J Biomech. 1980;13(5):417-21.
(Continued)

*Primary Examiner* — Tri T Ton
(74) *Attorney, Agent, or Firm* — Bret E. Field; Bozicevic, Field & Francis LLP

(57) ABSTRACT

A device for assessing changes in erythrocyte deformability, such as erythrocyte sickling tendency in a controlled hypoxic atmosphere, comprising: an at least partially transparent inner wall, an at least partially transparent outer wall extending parallel with the inner wall, wherein a gap is present between the inner and outer walls for receiving a blood sample, wherein one of said walls is movable parallel to and relative to the other one of said walls so as to exert a shear force to the sample in the gap, a light source arranged to emit light in a perpendicular direction through overlapping transparent parts of the inner and outer walls, a camera arranged to observe the light from the light source after it is emitted through said transparent parts of the inner and outer walls in order to detect and assess a diffraction pattern therein when a blood sample is present in said gap and the movable wall is being moved, and an oxygen sensor arranged to be in contact with the blood sample in the gap between the inner and outer walls and to measure the oxygen concentration in the blood sample when the blood sample is present in said gap and the movable wall is being moved.

(Continued)

The device is in particular useful for research and development in the field of sickle cell disease and the efficacy of medication and treatments.

20 Claims, 4 Drawing Sheets

(58) Field of Classification Search
USPC .......................................... 436/68, 250, 356
See application file for complete search history.

(56) References Cited

OTHER PUBLICATIONS

Sorette et al., Ektacyometric Measurement of Sickle Cell Deformability as a Continuous Function of Oxygen tension, Blood, 69(1): 316-323, 1987.
Shin et al., Laser-diffraction slit rheometer to measure red blood cell deformability, Review of Scientific Instruments 75(2): 559-561, 2004.
Hardeman et al., Laser-assisted optical rotational cell analyser (L.O.R.C.A.), Clinical Hemorheology, 14(4): 605-618, 1994.
Dabhi et al., Smart oxygen cuvette for optical monitoring of dissolved oxygen in biological blood samples, Proceedings of SPIE, 7576, Feb. 11, 2010, 75761B.

* cited by examiner

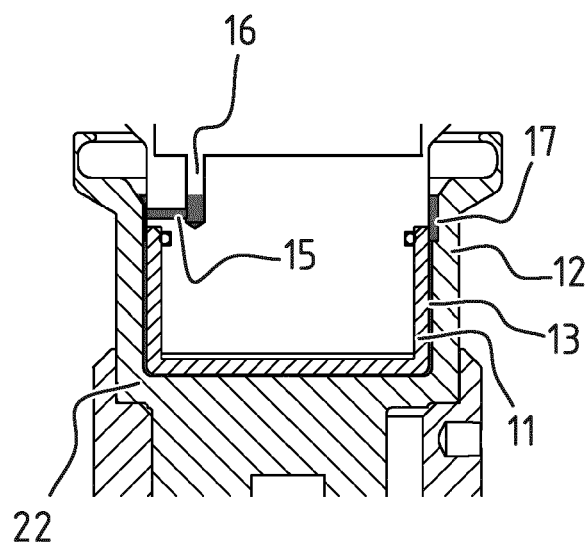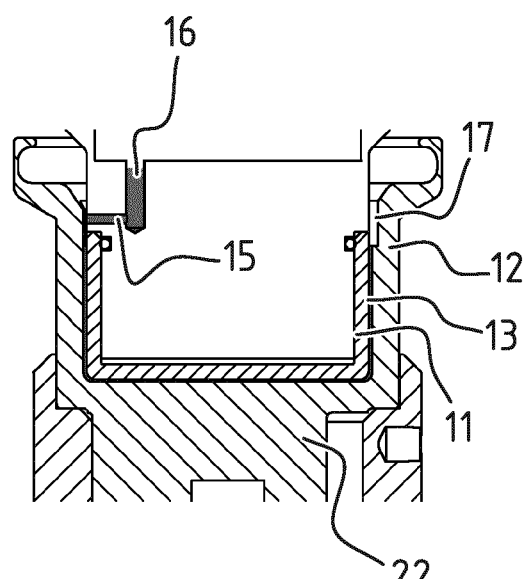
FIG. 3A    FIG. 3B
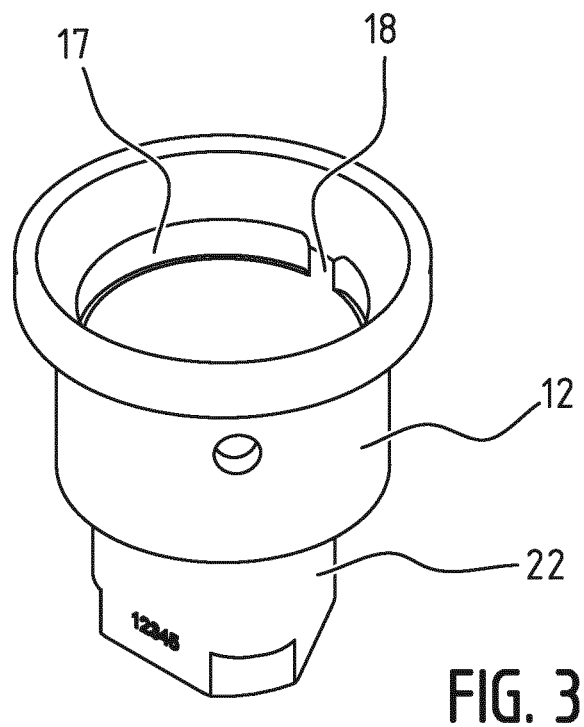
FIG. 3C

DEVICE FOR ASSESSING CHANGES IN ERYTHROCYTE DEFORMABILITY, SUCH AS ERYTHROCYTE SICKLING TENDENCY

The invention relates to a device for assessing changes in erythrocyte deformability, such as erythrocyte sickling tendency, comprising an at least partially transparent inner wall, an at least partially transparent outer wall extending parallel with the inner wall, wherein a gap is present between the inner and outer walls for receiving a blood sample (which may also be a diluted blood sample, for instance in a medium with a defined viscosity), wherein one of said walls is movable parallel to and relative to the other one of said walls so as to exert a shear force to the sample in the gap, a light source arranged to emit light in a perpendicular direction through overlapping transparent parts of the inner and outer walls, and a camera or a light sensor array arranged to observe the light from the light source after it is emitted through said transparent parts of the inner and outer walls in order to detect and assess a diffraction pattern therein when a blood sample is present in said gap and the movable wall is being moved.

Such a device is disclosed in US patent application publication US 2011/0318773 A1 and in the public academic Ph.D. thesis "Engineering developments in hemorheology", Universiteit van Amsterdam 2002, by J. G. G. Dobbe, in Paragraph 1.4.1 (pages 12-15), which are both incorporated herein by reference. These devices are known as ektacytometers.

Deformability is an important quality of red blood cells (RBCs) also called erythrocytes. The small capillaries in the human blood system are smaller than the circumference of an RBC. To pass, the cells must be deformable. Many RBC disorders have a negative effect on the deformability. Spherocytosis and Stomacytosis are for example two RBC membrane disorders that affect the deformability of RBC. Also RBC enzyme disorders like G6PD and PKD and hemoglobinopathies like Thalassemia and sickle cell disease have an effect on the deformability of RBC's under different circumstances.

An ektacytometer is an instrument derived from a Couette viscosimeter that measures the deformability of RBC through its diffraction pattern. In this instrument, the RBC's are placed under shear force and if the viscosity of the inside of the RBC matches that of the shear medium, the membrane of the cell will show the phenomenon called tank-treading. The membrane will rotate around the inside cytoplasm of the cell. This causes the cells to orientate in the shear field. A laser or other light beam traversing these cells in the suspension will project a diffraction pattern that is affected by the collective orientation of the cells. The diffraction bending of the light beam will be larger across the shorter edges and less across the longer edges of the oriented cells. Thus giving a measure of the deformability of the cells. If the cell membrane is a rigid sphere as typical in patients suffering spherocytosis, the cells will be less able to deform and orient in relation to the direction of the shear force and show a diffraction pattern that is less pronounced.

In sickle cell disease, due to a genetic mutation, affecting the red blood cell's (RBC) oxygen carrying molecule hemoglobin, the RBCs may become rigid and even sickle shaped from polymerization of the hemoglobin molecules within the cell. This polymerization is dependent on many parameters among which the oxygen level is the most significant. Time, cell hydration, hemoglobin concentration in the cell also are known to have an influence on the polymerization.

Sickle cell disease is a hereditary genetic disorder where one base-pair (single nucleotide substitution) in the genome is different. If a person only has inherited the trait from one of its parents, it will generally lead a symptom free life. In addition to a symptomless life, the trait results in some protection against malaria. If however, the sickle cell trait or point mutation is inherited from both parents the person is likely to develop symptoms related to sickle cell disease. Symptoms are rigidifying of the red blood cells under low oxygen condition that can stop or limit the blood flow in organs resulting in infarctions, organ damage and anemia.

Babies up to several months old will not show the symptoms of the disorder because their blood still contains hemoglobin-F (HbF), this fetal form of hemoglobin that does not polymerize under low oxygen conditions. There are also some blood disorders like Alpha-Thalassemia and persistent HbF that give some protection against the so-called sickling of the RBCs. Other blood disorders on combination with the Sickle cell trait inherited from only one parent may still contribute to the Sickle cell disease related spectrum of symptoms. Typically, the same point mutation results in a wide range in severity across the individual patients. At one end of the spectrum some patients only need to pay attention to their lifestyle avoiding stress, cold, heat, infection and maintain a sufficient level of hydration. At the other end of the spectrum patients are permanently dependent on blood transfusion and an array of medicines to treat the symptoms. Because it is a genetic disorder, only stem-cell replacement is expected to be able treat the cause.

The only current FDA approved medication for SCD is Hydroxyurea. Hydroxyurea has a range of effects among which an increase of HbF content in the RBC. It also has unwanted side effects, among which myelosuppression, requiring close monitoring of the patient and fine-tuning of the dose.

Beside the currently used Hydroxyurea, there are several substances being investigated for their efficacy in treating SCD. These novel agents for example induce an increase of HbF, or modify the oxygen affinity of the hemoglobin for O2, or reduce the dehydration of the RCB. Some combinations of medication are known to show a compounding effect to the effect of hydroxyurea.

An instrument capable of assessing the sickling susceptibility of a patients' RBCs can be used to find an acceptable dose as a balanced risk between side-effects and required therapeutic anti sickling effect.

Also in the case of partial stem cell replacement, the sickling tendency of a patient needs to be monitored to assess from the reduction in sickling tendency whether a sufficient number of stem cells have been replaced, and whether over longer periods of time the new stem cells continue to deliver their share in the blood production.

The basic test to observe the sickling of SCD cells is by adding a substance to the blood sample that binds all present oxygen, then fixate the cells and observe the result under a microscope. This method is limited because it does not measure at which oxygen pressure the sickling is induced. It does however measure the number of sickled cells. It also requires the fixation of the result and preparation of sample for subsequent microscopic observation, and counting the percentage of sickled cells.

An improved method would be to change the gas atmosphere around the fluid containig the cells and continuously observe through a microscope at which oxygen level the cells sickle. A limitation of this method is the diffusion time of the controlled ambient gas atmosphere diffusing into the RBC.

Another method to control the oxygen tension in the sample was published by Johnson in 1985 by mixing deoxygenated fluid with an oxygenated fluid and adding the sample separately or already mixed with the oxy and deoxy fluid. A limitation of this method is again the uncertainty of the actual resulting oxygen level in the mixture. Also oxygen diffusion or buffering in the tubing will play a role. Another limitation of this mixing method is related to the difference in reaction time between the polymerization which is fast compared to the melting of the hemoglobin polymers in the cell.

For optimal accuracy, it would be preferable to measure the oxygen pressure at or near the place where the sickling occurs and is measured. The standard solution to measure oxygen in a fluid is by the use of a so called Clark-electrode. Such an electronic sensor requires electrical connections and a flow of the sampled fluid around the electrode. A Clark-electrode is relatively slow in its measured response to a change in oxygen pressure which makes it not suitable for the measurement of RBC sickling tendency.

Red blood cells inside a living body are continuously subjected to a range of shear stresses. This physiological circumstance may be to influence the exchange of oxygen and the polymerization of the hemoglobin. Therefore, it is important to be able to control these shear conditions in an analytical instrument that is for the investigation of sickle cells.

According to the invention the device further comprises an oxygen sensor arranged to be in contact with the blood sample in the gap between the inner and outer walls and to measure the oxygen concentration in the blood sample when the blood sample is present in said gap and the movable wall is being moved.

Preferably said gap is shielded from the environment of the device, and the device comprises an supply opening for feeding a gas which is hypoxic, normoxic or hyperoxic to said gap, when the blood sample is present in said gap and the movable wall is being moved.

Said walls preferably extend vertically upright, such that oxygen is allowed to escape from the sample in the gap at the top end of the gap.

Said light source preferably is a laser. Preferably said light source is enclosed by the inner wall.

In a preferred embodiment said device comprises more than one light source and camera set at different heights of said gap and/or more than one oxygen sensor at different heights of said gap.

In another preferred embodiment said device comprises more than one light source, each having a different wave length.

The dimensions of the device are preferably chosen such that said movement of said wall causes a Couette flow in said sample.

Although it is feasible that the inner and outer walls of the device are formed by flat plates, in the preferred embodiment said device is a concentric cylinder type ektacytometer, wherein said inner wall is formed by an inner cylinder and said outer wall is formed by an outer cylinder. Preferably said inner wall is static and said outer wall is movable. Preferably said oxygen sensor extends on the inner surface of the outer wall.

Said oxygen sensor preferably comprises an luminophoric element in contact with the blood sample, comprising a luminophore, the luminescent property of which depends on the oxygen level of the blood sample in contact with the element, and a light sensor arranged to measure the intensity of the light emitted from said luminophore. Suitable luminophores are for instance disclosed in international patent publication WO 02/103334, which is incorporated by reference herein for that purpose.

In a preferred embodiment said luminophoric element extends on the inner surface in the form of a dot, and intermittently passes said light sensor by said movement of the wall. In another preferred embodiment said luminophoric element extends on the inner surface in the form of a line, and continuously passes said light sensor by said movement of the wall. In a still further preferred embodiment said luminophoric element extends on the wall in the form of two of said lines, one above the camera and one below the camera, such that an intermediate oxygen concentration of the blood sample at the height of the camera can be calculated from two light sensor measurements.

Preferably said light sensor is arranged outside the outer wall, said device preferably comprising a glass fiber, at its one end extending in the vicinity of the outer wall at the height of the luminophore and at its other end extending near the light sensor, said glass fiber being arranged to transport the light from the luminophore to the light sensor.

Preferably near the top end of said gap an overflow arrangement is present in said walls, such that the vertical height of the blood sample in said gap is maximized at a predetermined height.

Furthermore means are preferably present for determining the light absorption in relation to the oxygen level of the sample, by measuring the reflection of, or the transmission through, the sample in the gap at one or more predefined wavelengths between 400 nm and 1000 nm.

The invention also relates to a method for assessing erythrocyte deformation tendency, such as erythrocyte sickling tendency. The device is in particular useful for research and development in the field of sickle cell disease and the efficacy of medication and treatments. In order to increase or reduce the sickling effect of blood cells, dedicated agents may be added to the sample, for instance an agent to increase or decrease the pH or the osmotic value, or a potential medication, or a medication acting on the oxygen affinity of the hemoglobin molecule. Also the device is particular useful for monitoring the efficacy of stem cell transplants.

Preferably said gap is substantially shielded from the environment of the device, and a gas which is hypoxic, normoxic or hyperoxic is fed to said gap, wherein the gas is preferably nitrogen or a mixture comprising different gasses, such as carbon monoxide, carbon dioxide or nitrogen monoxide.

The invention will be elucidated by means of preferred embodiments, with reference to the drawings, in which.

Figure 1:
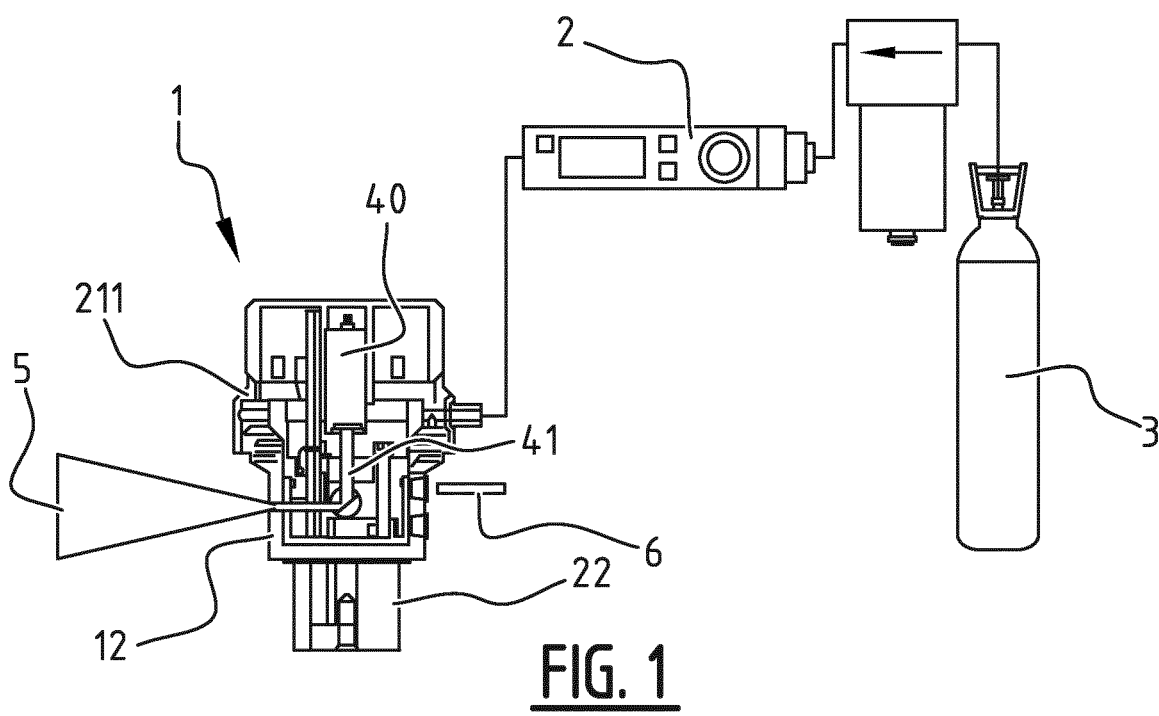
FIG. 1 is a schematic view of a system for assessing erythrocyte deformation tendency, such as erythrocyte sickling tendency.
Figure 2:
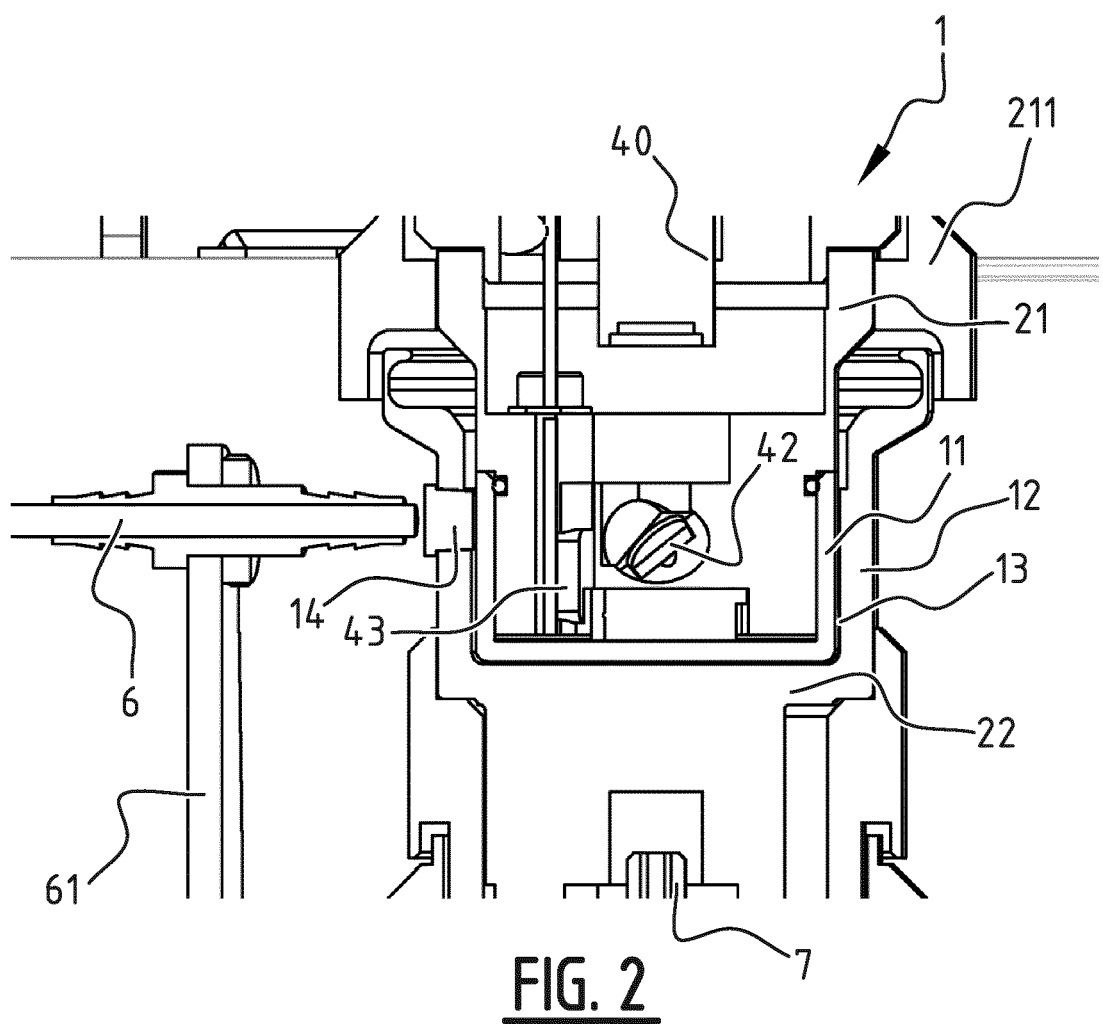
FIG. 2 is a cross section of a device for use in the system of FIG. 1.
Figure 4:
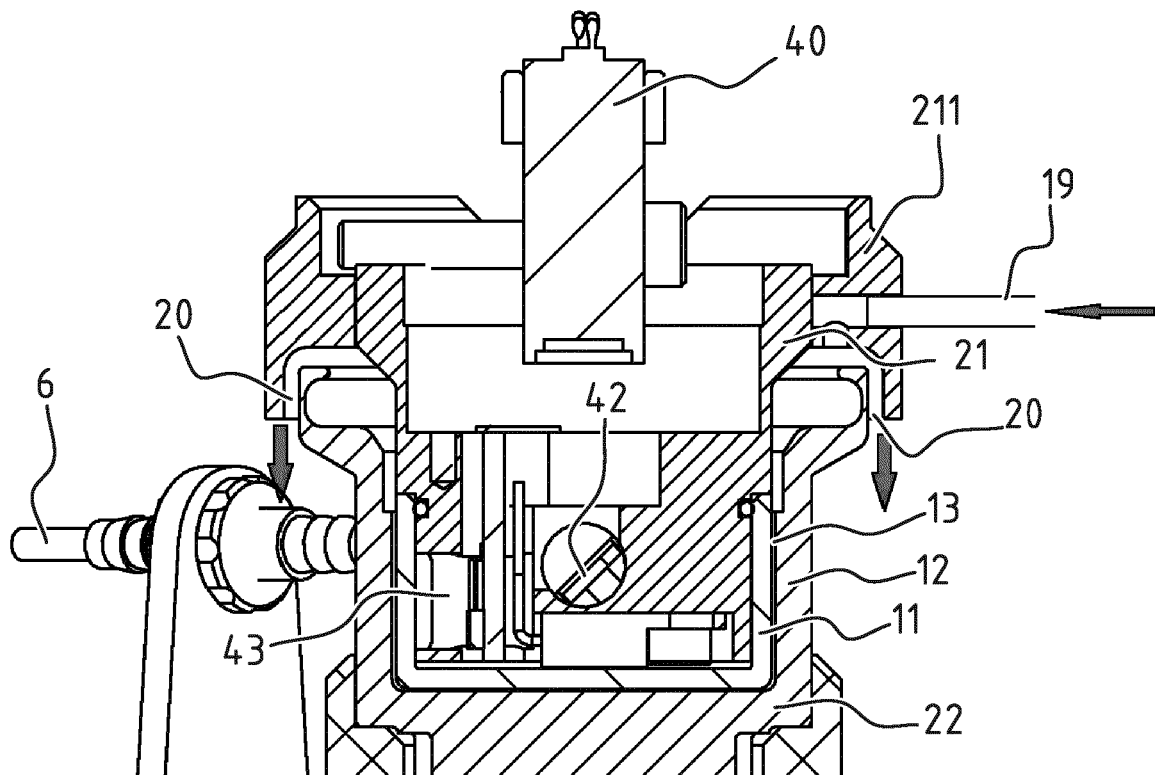
Figure 5:
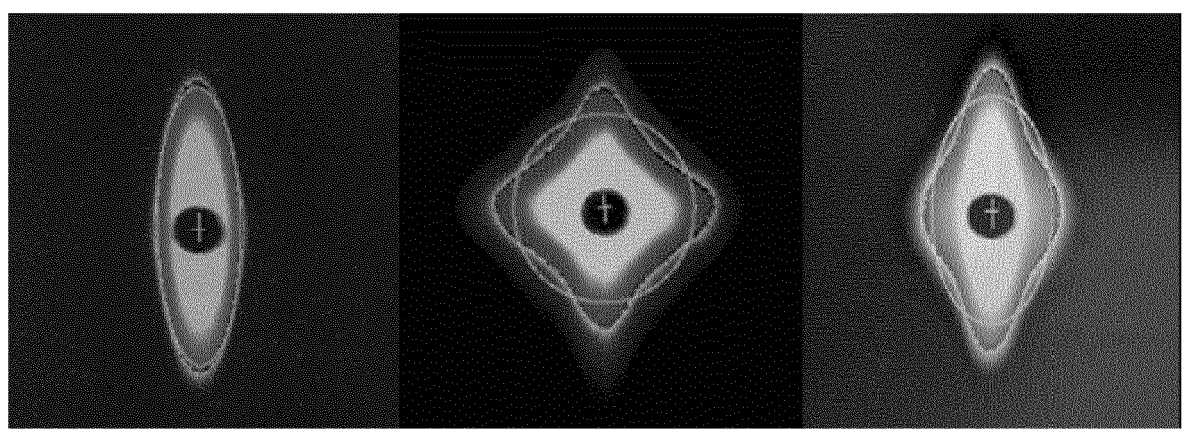
Figure 6:
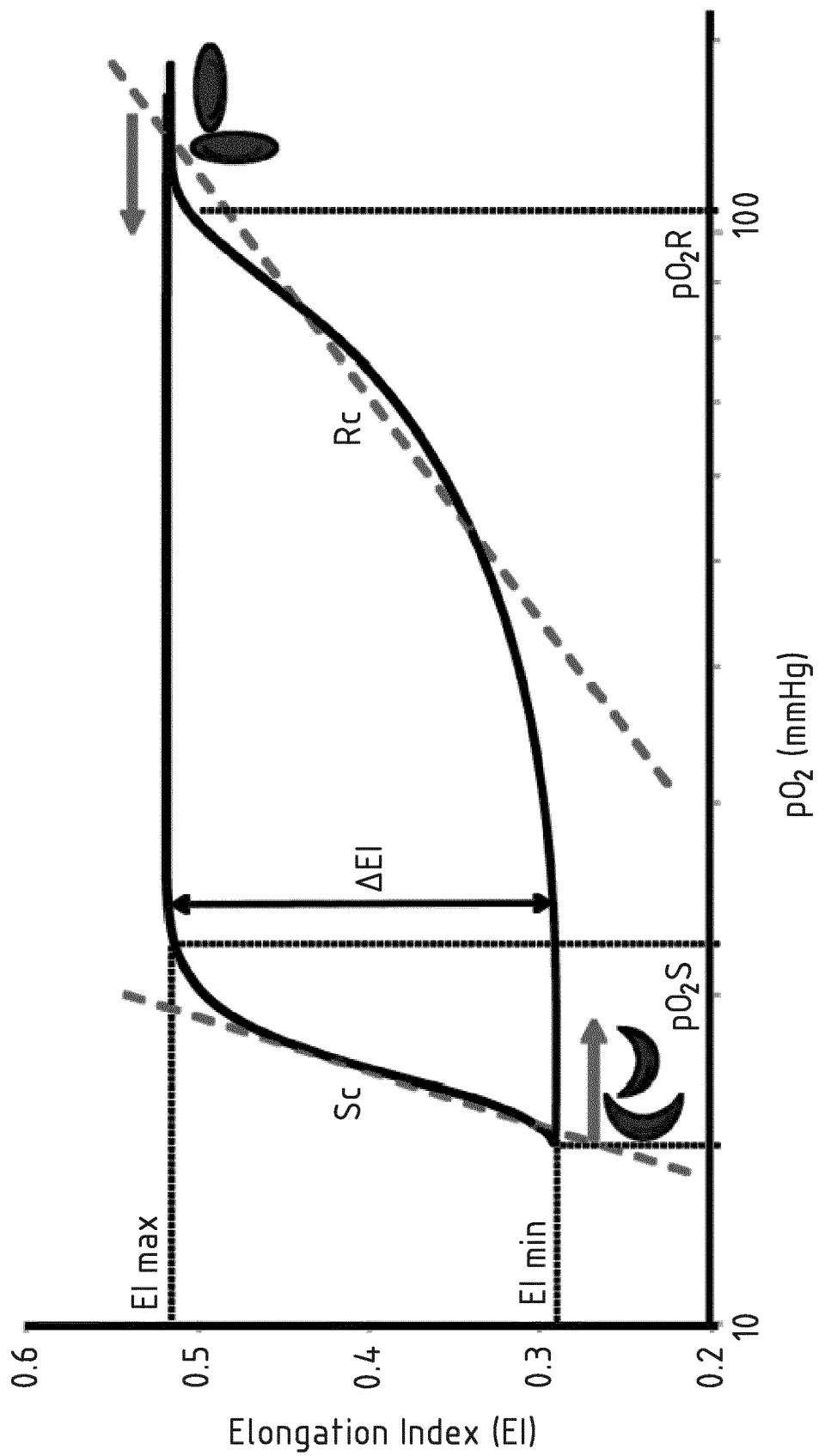

FIGS. 3A/B are cross sections of a detail of the device of FIG. 2, and FIG. 3C is a presepctive view of a detail of the device of FIG. 2, illustrating a blood sample level maximizing arrangement;

FIG. 4 is a cross section of the device of FIG. 2, illustrating supply and discharge of an oxygen free gas to the blood sample;

FIG. 5 are picture showing the diffraction pattern of normal and sickled blood cells;

FIG. 6 is a graphic representation of an example of the relationship between the elongation index (EI) as derived from the diffraction patterns as shown in FIG. 5 and the oxygen concentration (pO$_2$) in blood cells of a sickle cell patient during an exemplary assessment using the system of FIG. 1.

With reference to FIGS. 1 to 4, the system comprises an ektacytometer device 1, which is connected to a gas supply controller device 2, which is connected to a gas supply source 3, such as a gas tank. The gas controller device 2 may control the flow of gas in reaction to the measured oxygen level or other parameters measured in the ektacytometer device 1.

The ektacytometer device 1 comprises a stationary transparent inner cylinder 11 which is forms an outer wall of a metal bob 21 and a rotating mainly transparent external cylinder 12 which forms the upright wall of a rotating cup 22. The cup 22 is rotated by means of a motor 7 attached to the bottom of the cup 22. A stationary lid 211 is attached to the bob 21. As in a Couette system, the blood sample is analyzed in a small gap 13 between the two cylinders 11, 12. This gap may be between 3 µm and 1 mm, but should generally be smaller than 0.6 mm or even smaller than 0.3 mm.

Inside the stationary bob 21 a laser source 40 is vertically arranged, for emitting a laser beam 41 downwardly onto a mirror 42, which minors the laser beam 41 to a radially outward direction, through a through hole 43 in the bob 21 and then through the transparent inner cylinder 11, the blood sample in the gap 13 and through the transparent outer cylinder 12, onto a screen 5 that is observed by a camera (not shown) to observe the diffraction pattern.

The de-oxygenation or gas exchange of the sample is achieved at one side, along the upper end, of the gap 11, by creating a controlled atmosphere of for instance oxygen and/or other gases like for example nitrogen from gas tank(s) 3 in the room between the lid 211, the bob 21 and the cup 22 adjacent to the upper side of the gap 13. As shown in FIG. 4, a continuous flow of gas or a controlled gas mixture creates an atmosphere similar to the flowing gas. To that end a gas supply opening 19, to be connected with the gas supply source 3 and several gas exhaust openings 20 are present in the lid 211. Instead of oxygen another one or more gas components, like carbon-monoxide, carbon-dioxide, ozone, helium, so called radical oxygen species or acetone may be used.

Positioned in the circumference of the outer cylinder 12 there is a so called quenching luminophore element 14 of which the luminescence is dependent on the relative oxygen pressure in the blood sample. The luminophore element 14 comprises a luminophore with a gas permeable film extending on the inside of the outer cylinder 12 such that it is in contact with the sample, in order to accurately sense the oxygen level of the sample. It is positioned on the circumference such that it is on or near the height where the laser beam 41 traverses the cylinder 12 in order to accurately sense the oxygen level in the same rotating flow as that is causing the projected diffraction pattern. The luminophore element 14 is "read" without making contact by a glass fiber 6 illuminating the luminophore element 14 and through the same or another fiber capturing the luminescence. The glass fiber 6 is held in a stationary position by support member 61.

By positioning the luminophore element 14 perpendicular to the diffusion direction and at the same diameter as the rest of inner wall of the outer cylinder 12, there is no influence on the Couette flow and an accurate measurement of the oxygen pressure.

The luminophore element 14 may also be formed as a ring on the inside of the cylinder 12. It may also be formed as two rings in the cup, one placed above and one below the circumference from which the diffraction pattern is made. The actual oxygen or other gas level can be calculated from the two measured levels.

The luminophore element 14 is activated by light of a certain wavelength and its luminescence is read by a photosensor. A glass-fiber 6 may be between the activating light source and the sensor. The same fiber 6 may be used between the luminophore element 14 and the photosensor.

With reference to FIGS. 3A-3C, a constant diffusion length from the top of the gap 13 to the lumiphore element 14 as part of the oxygen sensor is preferred so that each test run has the same system dynamics. To obtain this constant diffusion length at the top of the gap 13, a hole 15 is made connected to an aspiration system 16, as an overflow arrangement, to aspirate the sample surplus of fluid above the aspiration hole 15. To further improve the reproducibility of the sample surplus aspiration the inner wall above the gap 13 along the circumference 17 of the outer cylinder 12 has been enlarged for most of the circumference, except for one small surface 18. Capillary forces make the fluid prefer to retreat from the enlarged gap along the circumference 12 towards the smaller capillary space. When this gap is positioned in front of the aspiration hole 15 this makes it possible to accurately aspirate to the level of the capillary smaller gap 11.

As shown in FIG. 5, if a sickle cell RBC becomes rigid at a certain oxygen pressure this is visible as a change in the diffraction pattern, wherein the first picture shows the diffraction pattern of a normal cell (EI=0.52), the second left pictures shows the diffraction pattern of a homozygote sickle cell fully deoxygenated (EI=0.29), and the third picture shows the diffraction pattern of a homozygote sickle cell oxygentated. In operation, the computer software fits an outline to the diffraction pattern, then calculates an elongation index (EI) at each oxygen concentration based on the length and width of the fitted ellipse: EI=(length−width)/(length+width).

FIG. 6 is a graphic representation of an example of the relationship between the elongation index (EI) as derived from the diffraction patterns as shown in FIG. 5 and the oxygen concentration (pO$_2$) in blood cells of a sickle cell patient during an exemplary assessment, wherein the oxygen concentration is subsequently decreased (upper line) and increased (lower line), representing for instance what happens during a great physical effort by a patient. From this graph several types of conclusions can be derived about the nature of the sickle cell tendency in the patient, such as the staring point and speed of formation (represented by the dotted line Sc) and the starting point and speed of recovery (represented by the dotted line Rc).

Measuring the oxygen affinity may be expressed as P50 of the RBC under shear condition.

The invention has thus been described by means of preferred embodiments. It is to be understood, however, that this disclosure is merely illustrative. Various details of the structure and function were presented, but changes made therein, to the full extent extended by the general meaning of the terms in which the appended claims are expressed, are understood to be within the principle of the present invention. The description and drawings shall be used to interpret the claims. The claims should not be interpreted as meaning that the extent of the protection sought is to be understood as that defined by the strict, literal meaning of the wording used in the claims, the description and drawings being employed only for the purpose of resolving an ambiguity found in the claims. For the purpose of determining the extent of protection sought by the claims, due account shall be taken of any element which is equivalent to an element specified therein. An element is to be considered equivalent to an element specified in the claims at least if said element performs substantially the same function in substantially the same way to yield substantially the same result as the element specified in the claims.

The invention claimed is:

1. A device for assessing changes in erythrocyte deformability, such as erythrocyte sickling tendency, comprising:
    an at least partially transparent inner wall,
    an at least partially transparent outer wall extending parallel with the inner wall,
    wherein a gap is present between the inner and outer walls for receiving a blood sample,
    wherein one of said walls is movable parallel to and relative to the other one of said walls so as to exert a shear force to the sample in the gap,
    a light source arranged to emit light in a perpendicular direction through overlapping transparent parts of the inner and outer walls, and
    a camera or a light sensor array arranged to observe the light from the light source after it is emitted through said transparent parts of the inner and outer walls in order to detect and assess a diffraction pattern therein when a blood sample is present in said gap and the movable wall is being moved,
    characterized in that said device further comprises:
    an oxygen sensor arranged to be in contact with the blood sample in the gap between the inner and outer walls and to measure the oxygen concentration in the blood sample when the blood sample is present in said gap and the movable wall is being moved.

2. The device of claim 1, wherein said gap is substantially shielded from the environment of the device, and the device comprises a supply opening for feeding a gas which is hypoxic, normoxic or hyperoxic to said gap, when the blood sample is present in said gap and the movable wall is being moved.

3. The device of claim 1, wherein said walls extend vertically upright, such that oxygen is allowed to escape from the sample in the gap at the top end of the gap.

4. The device of claim 1, wherein said light source is enclosed by the inner wall.

5. The device of claim 1, wherein the device comprises more than one light source and camera set at different heights of said gap.

6. The device of claim 1, wherein device comprises more than one light source, each having a different wave length.

7. The device of claim 1, wherein said device is a concentric cylinder type ektacytometer, wherein said inner wall is formed by an inner cylinder and said outer wall is formed by an outer cylinder.

8. The device of claim 1, wherein said inner wall is static and said outer wall is movable.

9. The device of claim 1, wherein said oxygen sensor extends on the inner surface of the outer wall.

10. The device of claim 1, wherein said oxygen sensor comprises an luminophoric element in contact with the blood sample, comprising a luminophore, the luminescent property of which depends on the oxygen level of the blood sample in contact with the element, and a light sensor arranged to measure the intensity of the light emitted from said luminophore.

11. The device of claim 1, wherein said luminophoric element extends on the inner surface in the form of a dot, and intermittently passes said light sensor by said movement of the wall.

12. The device of claim 1, wherein said luminophoric element extends on the inner surface in the form of a line, and continuously passes said light sensor by said movement of the wall, and preferably in the form of two of said lines, one above the camera and one below the camera, such that an intermediate oxygen concentration of the blood sample at the height of the camera can be calculated from two light sensor measurements.

13. The device of claim 1, wherein said light sensor is arranged outside the outer wall, said device preferably comprising a glass fiber, at its one end extending in the vicinity of the outer wall at the height of the luminophore and at its other end extending near the light sensor, said glass fiber being arranged to transport the light from the luminophore to the light sensor.

14. The device of claim 1, wherein near the top end of said gap an overflow arrangement is present in said walls, such that the vertical height of the blood sample in said gap is maximized at a predetermined height.

15. The device of claim 1, wherein furthermore means are present for determining the light absorption in relation to the oxygen level of the sample, by measuring the reflection of, or the transmission through, the sample in the gap at one or more predefined wavelengths between 400 nm and 1000 nm.

16. A method for assessing changes in erythrocyte deformability, such as erythrocyte sickling tendency, using a device according to claim 1.

17. The method of claim 16, wherein said gap is substantially shielded from the environment of the device, and a gas which is hypoxic, normoxic or hyperoxic is fed to said gap.

18. The method of claim 17, wherein the gas is nitrogen or a mixture comprising different gasses, such as carbon monoxide, carbon dioxide or nitrogen monoxide.

19. The device of claim 1, wherein the device comprises more than one oxygen sensor at different heights of said gap.

20. The device of claim 1, wherein the device comprises more than one light source and camera set at different heights of said gap and more than one oxygen sensor at different heights of said gap.

* * * * *